United States Patent [19]

Garner et al.

[11] Patent Number: 4,627,905

[45] Date of Patent: Dec. 9, 1986

[54] MONITOR ASSEMBLY FOR MONITORING ANODIC CORROSION PROTECTION OF CARBON STEEL VESSELS

[75] Inventors: Andrew Garner; Douglas L. Singbeil, both of Pointe Claire, Canada

[73] Assignee: Pulp and Paper Research Institute of Canada, Pointe Claire, Canada

[21] Appl. No.: 823,440

[22] Filed: Jan. 28, 1986

Related U.S. Application Data

[63] Continuation-in-part of Ser. No. 657,996, Oct. 5, 1984, abandoned.

[51] Int. Cl.$^4$ .................... G01N 27/46; C23F 13/00
[52] U.S. Cl. .................... 204/404; 204/1 T; 204/196; 204/286; 204/435; 204/400
[58] Field of Search .............. 204/17 C, 400, 404, 204/147, 148, 196, 197, 286, 297 R, 435

[56] References Cited

U.S. PATENT DOCUMENTS

| | | |
|---|---|---|
| 3,009,865 | 11/1961 | Mueller et al. .................... 204/147 |
| 3,462,353 | 8/1969 | Evert et al. .................... 204/196 |
| 3,660,264 | 5/1972 | Schuller .................... 204/197 |
| 3,980,542 | 9/1976 | Winslow et al. .................... 204/404 |
| 4,285,232 | 8/1981 | Garner .................... 204/404 |

*Primary Examiner*—T. Tung

*Attorney, Agent, or Firm*—Lawrence I. Field

[57] ABSTRACT

A monitor assembly is provided herein for monitoring the effectiveness of anodic protection of a carbon steel vessel containing a corrosive liquor, e.g. pulp digesters. The monitor has two identical carbon steel coupons mounted on a mount rod, one coupon being in electrical connection with the anodically protected vessel, the other being out of electrical connection with such vessel. A reference electrode is mounted on the same mount rod in such a way that the reference electrode, but not the mount rod, is wetted by the liquid contents of the carbon steel vessel. In this novel combination of elements, the mount rod, the metal components of a sealing gland and a metal spacer disc are made of any metal with sufficient mechanical and chemical stability to withstand the corrosive environment of the liquid contents of the carbon steel vessel and the mechanical stress. An electrically non-conductive sleeve and electrically non-conductive spacer elements are formed of any electrically non-conductive material having sufficient mechanical and chemical stability to withstand the corrosive environment of the liquid contents of the carbon steel vessel and the mechanical stress. The reference electrode is formed from any metal which provides a stable potential when exposed to the liquid contents of the carbon steel vessel.

15 Claims, 3 Drawing Figures

MONITOR ASSEMBLY FOR MONITORING ANODIC CORROSION PROTECTION OF CARBON STEEL VESSELS

This application is a continuation-in-part of Ser. No. 657,996, filed Oct. 5, 1984 now abandoned.

BACKGROUND OF THE INVENTION

(i) Field of the Invention

This invention relates to a monitor assembly for monitoring any possible corrosion and/or the corrosion protection and potential of a carbon steel vessel containing a caustic liquor. More particularly it is directed to such a monitor assembly for use in carbon steel vessels used in the wood pulp industry which contain pulping liquor and which could be protected from corrosion by anodic protection.

(ii) Description of Prior Art

Carbon steel is known to be generally resistant to corrosion in caustic solutions due to build-up thereon of passive films. However, such passive films are susceptible to localized breakdown or to uniform corrosion, depending on the electrochemical potential exerted on the carbon steel by the caustic solution. Kraft or soda-process pulping liquors generally contain oxidants, e.g. polysulphides and organic species, which influence the corrosion potential of a carbon steel vessel and can cause localized corrosion in the form of caustic stress corrosion cracking or uniform corrosion.

Similar forms of corrosion have also been observed in the Bayer process which is used in the aluminum industry to refine Bauxite ore into a purer form of alumina.

The corrosion environment in vessels used in the pulp industry, e.g. kraft or soda pulp digesters and white liquor clarifiers, is alkaline with concentrations of NaOH in the range 8 to 100 g/L, $Na_2S$ up to 40 g/L and $Na_2CO_3$ around 25 g/L. The common alloys of construction are carbon steels like A516 grade 70 or A285 type C. In a number of cases pulp digesters made from these steels have suffered from caustic cracking or from high rates of uniform corrosion, and have required repair or reconstruction at considerable cost.

One procedure heretofore used to control corrosion in such digesters, as well as in Bayer-process vessels, has been anodic protection. Many patents teach the concept of corrosion control by inducing passivity in the metal by anodic polarization techniques. With such a technique, the vessel to be protected against corrosion by a chemical contained therein is anodically polarized with respect to an inert cathode suspended in the corrosive liquid in the vessel. An electric current is passed between the metallic vessel and the inert cathode so as to maintain the electrical potential of the vessel in the passive region. The necessary electrical potential can be determined by means of an anodic polarization curve, or by controlled potential immersion testing, or by controlled potential stress corrosion testing. The passive region can be identified after such tests, thus providing data indicative of the potential range within which the vessel should be maintained in order to attempt to minimize corrosion.

Amongst the prior patents dealing with this technique are: Mueller and Watson, U.S. Pat. No. 3,009,865, Banks et al., U.S. Pat. Nos. 3,371,023 issued Feb. 7, 1968, 3,375,183 issued Mar. 26, 1968, 3,378,472 issued Apr. 16, 1968, 3,379,629 issued Apr. 23, 1968, and 3,409,526 issued Nov. 5, 1968; Hoey, U.S. Pat. No. 3,442,779 issued May 6, 1969; and Hulthe, U.S. Pat. No. 4,036,716 issued July 19, 1977.

In order to carry out constant-potential anodic protection successfully, a means of measuring the vessel potential is essential and a reference electrode is used for this purpose. Many common reference electrodes, e.g. the silver/silver chloride electrode, are unsuitable for potential measurement in pulping liquors because they are poisoned by contact with reduced sulphur species, e.g. sulphide. However, it is well known that metallic silver, molybdenum and other metals can perform as a reproducible reference electrode in pulping liquors as taught by Every and Banks in U.S. Pat. No. 3,462,353, even though that patent more preferably teaches the use of metal/metal salt electrodes.

U.S. Pat. No. 4,285,232 by Garner, A. issued Aug. 25, 1981 teaches a method for monitoring the effectiveness of electrochemical protection by means of a monitor assembly which carries two corrosion coupons. The assembly is designed so that one coupon is protected, and the other is unprotected but otherwise identically exposed.

The electrochemical potential of a large carbon steel vessel, e.g. a pulp digester, is not uniform throughout the vessel but can vary substantially from place to place. Even when anodic protection is applied to such a vessel, the potential can be substantially non-uniform. The potential can vary because it is determined by three factors, each of which vary with position in the vessel. These factors are (a) liquor composition (b) the nature of film or deposit on the steel surface and (c) the proximity of the cathode in an anodic protection system. Because the potential is position-dependent, it is essential to monitor the potential at the same location as a monitor assembly which is used to monitor the effectiveness of protection. Potential monitoring and corrosion monitoring could be carried out using two separate probes one of which carries a reference electrode, and the other carries a corrosion monitor assembly. However, it is highly undesirable to locate two separate probe parts in close proximity on a carbon steel vessel, particularly in the case of a digester which is a pressure vessel and subject to strict codes and regulations. Moreover, it has not previously been proposed to mount the reference electrode on the same probe which carries the monitor assembly because of the difficulties of ensuring that only the reference electrode is wetted by the process lliquor, while the electrically connectable mount rod be maintained substantially dry.

SUMMARY OF THE INVENTION

(i) Aims of the Invention

Accordingly, one object of this invention is to provide a method for effective anodic protection of a carbon steel vessel subject to the action of a corrosive caustic-containing liquor in which the effectiveness of the protection is monitored and at the same location the potential is monitored.

Another object of this invention is the provision of an assembly to monitor caustic stress corrosion cracking and uniform corrosion, and potential, in an anodically protected carbon steel vessel.

A further object of this invention is the provision of a monitor assembly to monitor whether there is any development of caustic stress corrosion cracking and uniform corrosion in an unprotected carbon steel vessel.

(ii) Statement of the Invention

The present invention is embodied in a monitor assembly which is especially adapted for, but is not necessarily restricted to, monitoring the effectiveness of anodic protection against caustic cracking and uniform corrosion of a carbon steel vessel.

The monitor is a combination of a plurality of structurally and functionally interrelated elements. The first element is an electrically conductive mount rod, the mount rod being adapted to be electrically connectable through a voltmeter to the carbon steel vessel. An electrically non-conducting sleeve is disposed on the mount rod. An electrical sealing gland which is adapted to be connected to the sealing gland of a retractable probe and which is of conventional construction, is rigidly and fixedly secured to the mount rod, with the sleeve serving to isolate the mount rod electrically and to provide a pressure tight seal. A centrally-apertured, stainless steel spacer disc is disposed on the sleeve so as to be in electrical contact with a vicinal portion of the electrical sealing gland. A first carbon steel, centrally-apertured, monitor coupon is disposed on the sleeve so as to be in electrical contact with the electrical sealing gland through the intermediary of the stainless steel spacer disc. The coupon has a plurality of stamped patterns thereon which are so designed as to induce residual stress in the coupon. A first centrally-apertured, electrically non-conducting spacer element is disposed on the sleeve adjacent the first coupon so as to be in tight physical contact with the first coupon. A second carbon steel, centrally-apertured monitor coupon which is identical with the first monitor coupon is disposed on the sleeve adjacent the first spacer so as to be in tight physical contact with the first spacer element. A second centrally-apertured, non-conducting spacer element is disposed on the sleeve in tight physical contact with the second carbon steel coupon. Finally, a reference electrode is detachably but securely disposed on the mount in electrical contact with the mount so that while the reference electrode is wetted by the process liquor, the mount rod cannot be wetted by process liquor.

In this novel combination of elements, the mount rod, the metal components of the sealing gland and the metal spacer disc are made of any metal with sufficient mechanical and chemical stability to withstand the corrosive environment of the liquid contents of the carbon steel vessel and the mechanical stress. The electrically non-conductive sleeve and the electrically non-conductive spacer elements are formed of any electrically non-conductive material having sufficient mechanical and chemical stability to withstand the corrosive environment of the liquid contents of the carbon steel vessel and the mechanical stress. The reference electrode is formed from any metal which provides a stable potential when exposed to the liquid contents of the carbon steel vessel.

(iii) Other Features of the Invention

In one embodiment of this invention the mount rod and/or the stainless steel spacer disc may be formed of Type 316 stainless steel.

In another embodiment of the invention, the sleeve and/or the electrically non-conductive spacer elements may be formed of polytetrafluoroethylene, or of a filled polytetrafluoroethylene resin known by the Trade Mark of RULON A.

In still another embodiment of this invention, the electrical sealing gland may have the following structure: It comprises a body having a first component provided with suitable connections, preferably threaded, at each end thereof. One end of the first component serves rigidly to secure the sealing gland to a retractable probe. The other end of the first component is threaded and secured rigidly to a hollow, threaded, cylindrical second component, i.e. a threaded cap of the sealing gland. The third component is a non-threaded cylinder, disposed between the first component and the second component, and through which the sleeve fits. This serves to compress the sleeve into tight sealing contact with the sealing gland. The second component, namely the threaded cap, is thus in electrical contact with the first component. When the second component is rotated, it moves the non-threaded cylinder to constrain the compression fitting and effect the seal. The second component is in electrical contact with the stainless steel spacer disc. The electrical sealing gland likewise may be formed from a stainless steel. e.g. Type 316 stainless steel.

The carbon steel coupons are preferably formed of the same carbon steel as the anodically protected carbon steel vessel and may be either substantially rectangular or substantially circular in shape. Preferably, they are provided with a radially arranged stamped pattern, preferably a cold stamped pattern, so designed as to induce residual stress in the coupon. They are preferably designed to fit through a valve disposed in the vessel, the hole for the valve meeting, e.g. ASME code standards, so that the coupons would be $1\frac{1}{4}''-1\frac{1}{2}''$ in diameter. They are preferably $1/16''-\frac{1}{8}''$ thick.

The reference electrode is preferably formed from silver or molybdenum or stainless steel. Preferably it is in the form of a cylinder, having an internally threaded well, by means of which it may be threadedly secured to the threaded end of the stainless steel mount.

BRIEF DESCRIPTION OF THE DRAWINGS

In the accompanying drawings.

Figure 1:
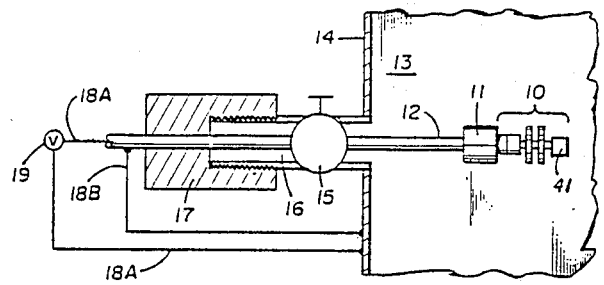
FIG. 1 is a schematic representation of the monitor of one embodiment of this invention mounted on a retractable probe used in the interior of a carbon steel vessel.

DESCRIPTION OF PREFERRED EMBODIMENTS (i) Detailed Description of FIG. 1

As seen in FIG. 1, the monitor 10 of one embodiment of this invention is screw mounted to a metallic probe-head 11 which is weld-connected to an electrically conductive hollow rod 12 and adapted to be moved by rod 12 into and out of the interior 13 of the carbon steel vessel 14 through a valve 15. When the monitor 10 is withdrawn through valve 15 into the holding chamber 16, the valve 15 can be closed and the monitor removed by unscrewing the packing gland 17. An insulated, electrically conductive wire 18A runs through the centre of rod 12 to connect the reference electrode 41 through a voltmeter 19 to the carbon steel vessel 14. A second electrically conductive wire 18B serves to connect the rod 12 to the carbon steel vessel 14.

The probe-head 11 and monitor 10 are of a size that can pass through valve 15. The size of valve 15 is determined by strict codes and regulations. Under ASME codes, a valve 15 with an outside diameter of 2″ or less is preferred since the fitting of larger valves requires more complex procedures. Consequently the maximum diameter of probe 11 and monitor 10 is between about 1⅛" and about 1¼".

Figure 2:
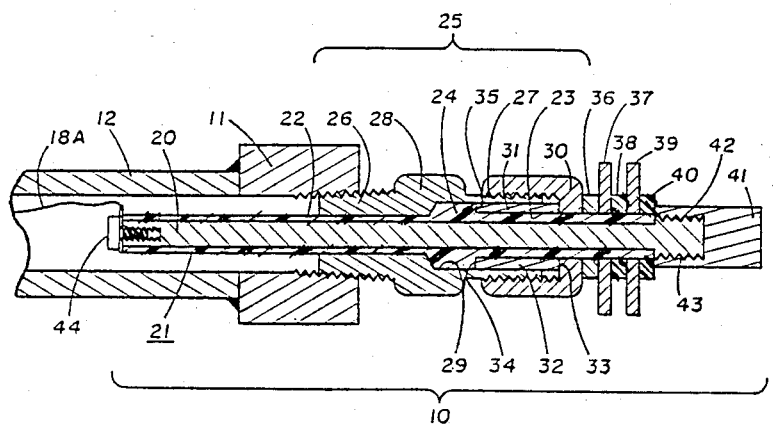
FIG. 2 is a central longitudinal cross-sectional view of a monitor constructed according to one embodiment of this invention.

(ii) Detailed Description of FIG. 2

As shown in FIG. 2, the monitor 10 includes a mount rod 20, which may be made of any metal which has sufficient mechanical and chemical stability to withstand the corrosive liquid environment within the carbon steel vessel and to withstand the mechanical stress, and which can be electrically and mechanically connected to the protected equipment to measure the electrochemical potential of the vessel. It is made from a stainless steel, preferably Type 316 stainless steel.

Close-fittingly disposed around mount rod 20 is a sleeve 21 formed of an electrically non-conductive material. While the sleeve may be formed of any electrically non-conducting material having sufficient mechanical and chemical stability to withstand the liquid corrosive environment within the carbon steel vessel and the mechanical stress, it preferably is formed of TEFLON (the Trade Mark for polytetrafluoroethylene of DuPont), or formed of a filled polytetrafluoroethylene resin known by the Trade Mark of RULON A. Sleeve 21 is formed with a fore portion 22, an aft portion 23 and a central enlarged block 24, whose purpose will be explained hereinafter. Sleeve 21 and mount rod 20 are of sufficient length that they extend into probe head 11 so that mount rod 20 is electrically insulated from probe head 11 and from hollow rod 12.

The sleeve 21 is encased by a conventional, commercially available electrical sealing gland, shown generally as 25. While any such conventional electrical sealing gland may be used, one embodiment thereof is the particular structure shown and now to be described.

The electrical sealing gland 25 includes a first hollow component having a threaded nose portion 26 which is screwed into probe head 11, a threaded tail 27 and a central hexagonal-in-cross-section block 28. The nose portion 26 is provided with a bore sized to accommodate the sleeve 21, while the tail portion 27 is provided with an enlarged internal diameter well 29 which is sized to accommodate the central enlarged block 24 of the sleeve 21. A cap 30 having an internally threaded forward well 31 is adapted to be secured to threaded tail 27. Disposed within well 31 and encircling sleeve 21 is a hollow, unthreaded cylindrical sleeve 32 having fore 34 and aft 33 engagement faces. When the cap 30 is secured into the tail 27, its inside face presses against face 33 which urges face 34 against face 35 of enlargement 24 of sleeve 21. This constrains the compression fitting and effects a seal.

The material out of which the electrical sealing gland is made may be made of any metal which has sufficient mechanical and chemical stability to withstand the liquid corrosive environment within the carbon steel vessel and to withstand mechanical stress. It may be made from a stainless steel, preferably from Type 316 stainless steel.

An electrically conductive, centrally apertured disc 36 is disposed on the sleeve 21 and is pressed into electrical contact with the exposed end of cap 30. The material out of which this disc 36 is made may be made of any metal which has sufficient mechanical and chemical stability to withstand the liquid corrosive environment within the carbon steel vessel and to withstand mechanical stress. It may be made from a stainless steel, preferably from Type 316 stainless steel.

A first carbon steel coupon 37 is disposed on the sleeve 21 to be in electrical contact with the end of the disc 36. The monitor coupon 37 is preferably made of the same carbon steel as the carbon steel vessel 14.

A first centrally apertured disc 38 formed of electrically non-conductive material is placed on the sleeve 21 in pressed contact against the face of first coupon 37. While the disc 38 may be any electrically non-conducting material having sufficient mechanical and chemical stability to withstand the liquid corrosive environment within the carbon steel vessel and the mechanical stress, it preferably is formed of TEFLON (the DuPont Trade Mark for polytetrafluoroethylene) or is formed of a filled polytetrafluoroethylene resin known by the Trade Mark or RULON A.

A second and identical carbon steel centrally apertured monitor coupon 39 is disposed on the sleeve 21, but this monitor coupon 39 is electrically isolated from the spacer 36 and the mount rod 20 by electrically non-conductive disc 38 and by non-conductive sleeve 21.

A second centrally apertured disc 40 formed of electrically non-conductive material is placed on the sleeve 21 in pressed contact against the face of coupon 39. While the disc 40 may be any electrically non-conducting material having sufficient mechanical and chemical stability to withstand the liquid corrosive environment within carbon steel vessel and the mechanical stress, it preferably is formed of TEFLON (the Trade Mark for polytetrafluoroethylene of DuPont) or is formed of a filled polytetrafluorethylene resin known by the Trade Mark of Rulon A.

A reference electrode 41, in the form of a solid metal cylinder, is removably but securely mounted in the mount rod 20 in electrical contact therewith, e.g. by having an internally threaded well 42 to secure it to threaded end 43 of the mount rod 20. The threaded end 43 of the mount rod 20 is larger in diameter than the internal aperture of the sealing gland 25 so that the mount rod 20 cannot be pushed through the sealing gland 25 by the force of the liquid contents of the carbon steel vessel 14. One end of reference electrode 41 is pressed against disc 40 to prevent wetting of mount rod 20 by the liquid contents of vessel 14. The reference electrode may be any suitable metal, e.g. as described in the above mentioned U.S. Pat. No. 3,462,353, but it preferably is stainless steel (e.g. Type 316 stainless steel) molybdenum or most preferably, silver.

Finally, an insulated, electrically conductive wire 18A is connected to mount rod 20, preferably by means of a screw 44 threaded into the fore end of mount rod 20. The wire 18A is connected to mount rod 20 so as to prevent electrical contact between the wire 18A and the electrically conductive hollow rod 12 or the probe head 11.

Figure 3:
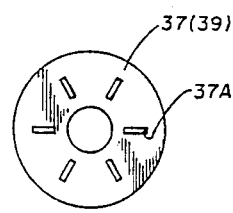
FIG. 3 is a plan view of a coupon used in the monitor.

(iii) Detailed Description of FIG. 3

As shown in FIG. 3, the monitor coupon 37(39) preferably has a radially arranged pattern, i.e. of cold stamped indentations 37A, which are so designed as to induce residual stress in coupon 37(39).

When the monitor probe 10 is fully assembled and attached to the probe head 11, the first monitor coupon 37 is in electrical contact with anodically protected vessel 14 by means of the probe head 11, the hollow rod 12 and the electrically conductive wire 18B (FIG. 1) and the second monitor coupon 39 is not in electrical contact with anodically protected vessel 14. Both the first monitor coupon 37 and the second monitor coupon 39 are in identical face-to-face contact with their respective spacers (38 or 40). The contact pressure is also identical. Consequently, all variables except for the anodic protection have been eliminated from the monitor coupons 37 and 39. The reference electrode 41 is in direct electrical contact with mount rod 20, which is electrically connected through a voltmeter 19 to the vessel 14 by means of the insulated, electrically conductive wire 18A. The voltmeter 19 is used to measure the electrical potential of the vessel. Furthermore, the reference electrode 41 is not in electrical contact with the anodically protected vessel 14, the sealing gland 25, or either of the monitor coupons 37 and 39.

(iv) Operation of the Preferred Embodiment

The effectiveness of the monitor assembly 10 in monitoring the effectiveness of anodic protection in a carbon steel pulp digester was confirmed by the following tests:

In a laboratory test, monitor coupons, made from A516 Grade 70 carbon steel, and a reference electrode, made from silver, were exposed for up to 1,940 hours to a typical synthetic kraft-process digester liquor which contained 40 g/L NaOH, 20 g/L $Na_2S$ and 20 g/L $Na_2CO_3$ at 110° C. Before the test the monitor coupons were preweighed and cold stamped to induce residual stress. Throughout the test a silver/silver chloride reference electrode, connected to the liquor via an elaborate salt bridge, was also used to monitor potentials.

Corrosion rate and stress corrosion cracking results for monitor coupons are shown in the following table:

| Coupon | Control Potential ($mV_{Ag}$) | Corrosion Rate | Stress Corrosion |
|---|---|---|---|
| A | Not controlled | 8.2 | No |
| B | +100 | 1.9 | No |
| C | Not controlled | — | No |
| D | −34 | — | Yes |

Results from the pair of coupons A and B show that an anodic protection potential of +100 $mV_{Ag}$ is effective in lowering the uniform corrosion rate from 8.2 to 1.9 mpy. Results from coupons C and D show that stress corrosion cracking occurs at a controlled potential of −34 $mV_{Ag}$, but no cracking occurs under free-corrosion (no potential-control) conditions in this particular liquor.

The potential of the silver electrode remained stable with respect to the silver/silver chloride electrode at a potential of −905 $mV_{Ag/AgCl} \pm 5$ $mV_{Ag/AgCl}$. Thus it was confirmed that silver is a suitable reference electrode material for use in kraft liquor.

We claim:

1. A monitor assembly for monitoring the effectiveness of anodic protection of carbon steel vessels comprising:
   (a) an electrically conductive mount-rod adapted to be electrically connected through a voltmeter to said carbon steel vessel;
   (b) an electrically non-conductive sleeve on said mount rod;
   (c) an electrical sealing gland encasing said sleeve;
   (d) a stainless steel apertured spacer disc mounted on said sleeve in electrical contact with said electrical sealing gland;
   (e) a first carbon steel coupon mounted on said sleeve in electrical contact with said stainless steel disc;
   (f) A first spacer element of electrically non-conductive material mounted on said sleeve adjacent to, in pressing contact with, said first carbon steel coupon;
   (g) a second carbon steel coupon identical to said first carbon steel coupon mounted on said sleeve adjacent to, and in pressing contact with, said first spacer element;
   (h) a second spacer element of electrically non-conductive material mounted on said sleeve adjacent to, and in pressing contact with, said second carbon steel coupon; and
   (i) a reference electrode detachably but securely mounted in direct electrical contact with, and on said mount rod so that said reference electrode, but not said mount rod is wetted by the liquid contents of said carbon steel vessel;

said mount rod, and said electrical sealing gland being made of any metal with sufficient mechanical and chemical stability to withstand the corrosive environment within the carbon steel vessel and the mechanical stress; said electrically non-conductive sleeve and said electrically non-conductive spacer elements being formed of any electrically non-conductive material having sufficient mechanical and chemical stability to withstand the corrosive environment with the carbon steel vessel and the mechanical stress; and said reference electrode being formed from any metal which provides a stable potential when exposed to the liquid contents of said carbon steel vessel.

2. The monitor assembly of claim 1 wherein said mount rod is formed of stainless steel.

3. The monitor assembly of claim 1 wherein said mount rod is formed of Type 316 stainless steel.

4. The monitor assembly of claim 1 wherein said sleeve is formed of polytetrafluoroethylene.

5. The monitor assembly of claim 1 wherein said sleeve is formed of a filled polytetrafluoroethylene resin.

6. The monitor assembly of claim 1 wherein said stainless steel spacer disc is formed of Type 316 stainless steel.

7. The monitor assembly of claim 1 wherein said spacer elements are apertured discs formed of polytetrafluoroethylene resin.

8. The monitor assembly of claim 1 wherein said spacer elements are apertured discs formed of a filled polytetrafluoroethylene resin.

9. The monitor assembly of claim 1 wherein said carbon steel coupons are apertured discs formed of the same carbon steel as said carbon steel vessels.

10. The monitor assembly of claim 1 wherein said carbon steel coupons are provided with an array of stamped indentations thereon to induce residual stress therein.

11. The monitor assembly of claim 1 wherein said carbon steel coupons are provided with an array of cold stamped indentations thereon to induce residual stress therein.

12. The monitor assembly of claim 1 wherein said reference electrode is a cylindrical block of silver threaddedly secured to said mount rod.

13. The monitor assembly of claim 1 wherein said electrical sealing gland comprises a body having a first component provided with suitable connection means at one end for rigid securement to a retractable probe and suitable connection means at the other end thereof for rigid securement to a hollow, threaded, cylindrical second component; and a third component comprising a non-threaded hollow open ended cylinder, disposed between said first component and said second component, and through which said sleeve fits, and serving to compress said sleeve into tight sealing contact with said electrical sealing gland.

14. The monitor assembly of claim 13 wherein said connection means on said first component and said second component comprises threads whereby when said second threaded component is rotated, it moves said non-threaded cylinder to constrain the compression fitting and to effect the seal.

15. In combination, a carbon steel vessel and a monitor assembly comprising:
(a) an electrically conductive mount rod adapted to be electrically connected through a voltmeter to said carbon steel vessel;
(b) an electrically non-conductive sleeve on said mount rod;
(c) an electrical sealing gland encasing said sleeve;
(d) a stainless steel apertured spacer disc mounted on said sleeve in electrical contact with said electrical sealing gland;
(e) a first carbon steel coupon mounted on said sleeve in electrical contact with said stainless steel disc;
(f) a first spacer element of electrically non-conductive material mounted on said sleeve adjacent to, in pressing contact with, said first carbon steel coupon;
(g) a second carbon steel coupon identical to said first carbon steel coupon mounted on said sleeve adjacent to, and in pressing contact with, said first spacer element;
(h) a second spacer element of electrically non-conductive material mounted on said sleeve adjacent to, and in pressing contact with, said second carbon steel coupon; and
(i) a reference electrode detachably but securely mounted in direct electrical contact with, and on said mount rod so that said reference electrode, but not said mount rod is wetted by the liquid contents of said carbon steel vessel;

said mount rod, and said electrical sealing gland being made of any metal with sufficient mechanical and chemical stability to withstand the corrosive environment within the carbon steel vessel and the mechanical stress; said electrically non-conductive sleeve and said electrically non-conductive spacer elements being formed of any electrically non-conductive material having sufficient mechanical and chemical stability to withstand the corrosive environment with the carbon steel vessel and the mechanical stress; and said reference electrode being formed from any metal which provides a stable potential when exposed to the liquid contents of said carbon steel vessel.

* * * * *